United States Patent [19]

Bays et al.

[11] Patent Number: 4,476,126

[45] Date of Patent: Oct. 9, 1984

[54] 1,2,4 TRIAZOZE AMINES AND THEIR PHARMACEUTICAL USE

[75] Inventors: David E. Bays; John W. Clitherow, both of Hertfordshire, United Kingdom

[73] Assignee: Glaxo Group Limited, London, England

[21] Appl. No.: 387,530

[22] Filed: Jun. 11, 1982

[30] Foreign Application Priority Data

Jun. 11, 1981 [GB] United Kingdom ................ 8117955
Jul. 22, 1981 [GB] United Kingdom ................ 8122605

[51] Int. Cl.$^3$ .................... A61K 31/45; C07D 403/10; C07D 403/14

[52] U.S. Cl. ............................. 424/248.56; 424/263; 424/267; 424/269; 544/82; 544/129; 544/124; 544/132; 546/187; 546/193; 546/194; 546/276; 546/256; 546/210; 548/266

[58] Field of Search ................ 544/82, 129, 124, 132; 546/187, 193, 194, 276, 256, 210; 548/266; 424/248.56, 263, 267, 269

[56] References Cited

U.S. PATENT DOCUMENTS 4,323,566 4/1982 Clitherow et al. ................ 544/124

Primary Examiner—Robert T. Bond
Attorney, Agent, or Firm—Bacon & Thomas

[57] ABSTRACT

This invention relates to compounds of the general formula (I)

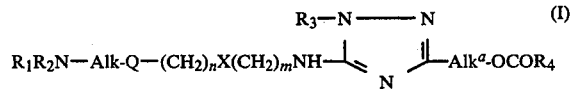

and physiologically acceptable salts, hydrates and bioprecursors thereof in which the substituents are defined later.

The compounds show pharmacological activity as selective histamine $H_2$-antagonists.

9 Claims, No Drawings

1,2,4 TRIAZOZE AMINES AND THEIR PHARMACEUTICAL USE

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in British Patent Specification No. 1,565,966 modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated quinea pig right atrium but do not modify histamine induced contractions of isolated gastrointestinal smooth muscle which are mediated via $H_1$-receptors.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

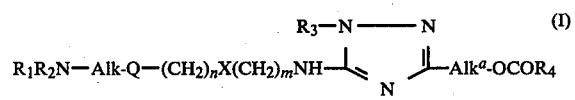

and physiologically acceptable salts, hydrates and bioprecursors thereof in which $R_1$ represents $C_{1-14}$ alkyl, cycloalkyl, alkenyl, alkynyl, aralkyl, heteroaralkyl, trifluoroalkyl or alkyl substituted by hydroxy, alkoxy, amino, alkylamino, dialkylamino or cycloalkyl; and $R_2$ represents hydrogen or $C_{1-4}$ alkyl; or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl e.g. methyl, groups or a hydroxy group and/or may contain another heteroatom, e.g. oxygen or sulphur;

Alk represents a straight or branched alkylene chain of 1 to 6 carbon atoms;

Q represents a furan or thiophen ring in which incorporation into the rest of the molecule is through bonds at the 2- and 5-positions, the furan or thiophen ring optionally bearing a further substituent $R_6$ adjacent to the group $R_1R_2N$-Alk; or Q represents a thiophen ring in which incorporation into the rest of the molecule is through bonds at the 2- and 4-positions, the thiophen ring optionally bearing a further substituent $R_6$ adjacent to the group $R_1R_2N$-Alk with the proviso that when the group $R_1R_2NAlk$ is in the 4-position then the group $R_6$ is in the 5- position; or Q represents a benzene ring in which incorporation into the rest of the molecule is through bonds at the 1- and 3- or 1- and 4-positions;

$R_6$ represents halogen or $C_{1-4}$ alkyl which may be substituted by hydroxy or $C_{1-4}$ alkoxy;

X represents oxygen, sulphur, —NH—, methylene or a bond;

n represents zero, 1 or 2; and m represents an integer from 2 to 5; with the proviso that when X represents —NH— then Q is a benzene ring;

$R_3$ represents hydrogen, alkyl, alkenyl, aralkyl, or $C_{2-6}$ alkyl substituted by hydroxy or alkoxy;

$Alk^a$ represents a straight or branched alkylene chain containing from 1 to 6 carbon atoms;

$R_4$ represents the group —$ZCOR_5$ where $R_5$ represents hydroxy or alkoxy or the group

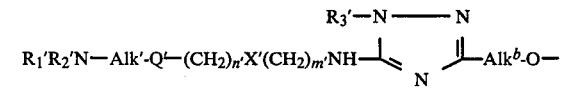

in which the symbols $R_1'$, $R_2'$, Alk', Q', n', X', m' and $R_3'$ have meanings which are as defined above for the symbols $R_1$, $R_2$, Alk, Q, n, X, m and $R_3$ respectively but which, in each case, may be the same as or different to the meaning of the latter symbol;

$Alk^b$ represents a straight or branched alkylene chain containing from 1 to 6 carbon atoms;

Z represents an alkylene chain containing from 1 to 16 carbon atoms optionally substituted by one or two $C_{1-3}$ alkyl groups and optionally containing a double or triple bond; or optionally interrupted by a hetero atom, e.g. oxygen or sulphur, or by a disulphide (S—S) group; or optionally interrupted by a cycloalkyl or a phenyl group, or Z represents a cycloalkyl or a phenyl group; or $R_4$ represents a $C_{1-6}$ straight or branched hydroxyalkyl group (optionally substituted by hydroxy or amino) or an aminoalkyl group (optionally substituted by amino, SH, $CO_2H$ or aryl, e.g. phenyl or 4-hydroxyphenyl).

The term "alkyl" as a group or part of a group means that the group is straight or branched and, unless otherwise stated, has preferably 1 to 6 carbon atoms, and in particular 1 to 4 carbon atoms, e.g. methyl or ethyl, and the terms "alkenyl" and "alkynyl" mean that the group has preferably 3 to 6 carbon atoms. The term "cycloalkyl" means that the group has 3 to 8 carbon atoms. The term "aryl" as part of an aralkyl group preferably means phenyl or substituted phenyl, for example phenyl substituted with one or more $C_{1-3}$ alkyl or alkoxy groups, or halogen atoms e.g. fluorine. The term "heteroaryl" as a group or part of a group means a 5 or 6 membered monocyclic ring containing 1 to 3 heteroatoms selected from oxygen, nitrogen and sulphur, e.g. thienyl, pyrrolyl, pyridyl, furyl or thiazolyl. The heteroaryl ring may be unsubstituted or substituted by $C_{1-3}$ alkyl, $C_{1-3}$ alkoxy, hydroxyalkyl, aminoalkyl, alkylaminoalkyl, dialkylaminoalkyl or halogen. For example the heteroaryl ring may be thienyl or furyl substituted by $C_{1-3}$ alkyl, aminoalkyl, alkylaminoalkyl, dialkylaminoalkyl or hydroxyalkyl, pyrrolyl substituted by $C_{1-3}$ alkyl, pyridyl substituted by $C_{1-3}$ alkyl, $C_{1-3}$ alkoxy, halogen or hydroxyalkyl or thiazolyl substituted by $C_{1-3}$ alkyl or hydroxyalkyl. The alkyl portion of a heteroaralkyl group is a straight or branched $C_{1-4}$ alkyl chain, and the heteroaryl ring is linked to the alkyl portion through a carbon atom. The term amino in the group $R_4$ means a primary amino group or an acylamino group in which acyl represents alkoxycarbonyl or aralkyloxycarbonyl e.g. benzyloxycarbonyl.

When Z is an alkyl-substituted alkylene chain there are preferably up to 10 carbon atoms in the backbone of the chain. When the alkylene chain Z contains a double or triple bond the total number of carbon atoms in the chain is preferably 2 to 6. When the alkylene chain Z is interrupted by a heteroatom or disulphide group there are preferably 2 to 10 carbon atoms in the chain. When the alkylene chain Z is interrupted by a cycloalkyl or a phenyl group the chain preferably contains 2 to 4 carbon atoms.

Preferred compounds of formula (I) are those in which $R_1$ represents $C_{1-8}$ alkyl (e.g. methyl, propyl, butyl or heptyl), $C_{1-4}$ alkyl substituted by a trifluoromethyl group (e.g. 2,2,2,-trifluoroethyl), $C_{2-4}$ alkyl substituted by hydroxy or a di $C_{1-3}$ alkylamino group (e.g. 3-hydroxypropyl or dimethylaminoethyl), $C_{5-7}$ cycloalkyl (e.g. cyclohexyl), $C_{3-5}$ alkenyl (e.g. allyl), phenyl $C_{1-3}$ alkyl (e.g. benzyl), or a heteroaryl $C_{1-3}$ alkyl group where the heteroaryl ring contains one heteroatom (e.g. 2-furylmethyl);

$R_2$ represents hydrogen or methyl; or $R_1R_2N$ represents a 5–7 membered ring optionally containing a double bond, an oxygen atom or an alkyl (e.g. methyl) substituent (e.g. piperidino, morpholino, 4-methylpiperidino, pyrrolidino, hexamethylenimino or tetrahydropyridino);

Alk represents methylene;

Q represents a benzene ring incorporated into the rest of the molecule through the bonds at the 1- and 3-positions; or a furan ring incorporated into the rest of the molecule through bonds at the 2- and 5-positions optionally bearing a substituent $R_6$ adjacent to the group $R_1R_2NAlk$ where $R_6$ is $C_{1-4}$ alkyl (e.g. methyl); or a thiophene ring incorporated into the rest of the molecule through bonds at the 2- and 4-positions with the substituent $R_1R_2NAlk$ in the 2-position; with the provisos that when Q is a benzene ring as just defined, then n is zero, X is oxygen, and m is 3 or 4; and when Q is a furan or thiophene ring as just defined, then n is 1, X is sulphur and m is 2, or X is oxygen and m is 3;

$R_3$ represents hydrogen or alkyl (e.g. methyl);

$Alk^a$ represents a straight or branched alkylene chain containing 1 to 4 carbon atoms; and $R_4$ represents a $C_{1-4}$ straight or branched hydroxyalkyl group (e.g. 1-hydroxyethyl) or a $C_{1-4}$ aminoalkyl group (in which the amino group is in the α-position relative to the ester moiety), optionally substituted by amino (as defined above), SH, $CO_2H$ or aryl, more preferably $C_{1-4}$ aminoalkyl in which the amino group is as defined above, or $R_4$ represents the group $-ZCOR_5$ where Z represents a cycloalkyl group (e.g. cyclohexyl) or an unsubstituted alkylene chain containing 1 to 16 carbon atoms, more particularly 1 to 10 carbon atoms, and $R_5$ represents hydroxy or alkoxy; or Z represents a phenyl group or an unsubstituted alkylene chain containing 1 to 16 carbon atoms, more particularly 1 to 10 carbon atoms optionally containing a double bond or optionally interrupted by either a heteroatom (e.g. oxygen) or a disulphide group or a phenyl group, and $R_5$ represents a group

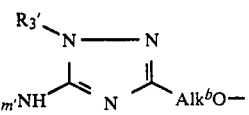

$$R_1'R_2'NAlk'Q'(CH_2)_n'X'(CH_2)_m'NH$$

in which the symbols $R_1'$, $R_2'$, $Alk'$, $Q'$, $n'$, $X'$, $m'$ and $R_3'$ have meanings which are as defined above for the preferred meanings for the symbols $R_1$, $R_2$, $Alk$, $Q$, $n$, $X$, $m$ and $R_3$ respectively but which, in each case, may be the same as or different to the meaning of the latter symbol, and $Alk^b$ represents a straight or branched alkylene chain containing 1 or 2 carbon atoms.

When $R_4$ represents a substituted aminoalkyl group the group $R_4CO$ is more preferably glycyl, alanyl, isoleucyl, leucyl, valyl, aspartyl, glutamyl, cysteinyl, lysyl, seryl, threonyl, phenylalanyl or tyrosyl.

More preferably $R_1$ and $R_2$ are both methyl or, together with the nitrogen atom to which they are attached form a pyrrolidino, piperidino or hexamethylenimino group;

Alk represents methylene and $R_3$ is hydrogen or methyl and; either n is zero, X is oxygen, m is 3 or 4 and Q is a benzene ring linked through the 1- and 3-positions; or n is 1, X is sulphur, m is 2 and Q is furan linked through the 2- and 5-positions with optionally a methyl substituent on the carbon atom adjacent to the group $R_1R_2NCH_2-$ or Q is a thiophen ring linked through the 2- and 4-positions with the group $R_1R_2NCH_2-$ in the 2-position; with the proviso that when Q is other than a benzene ring then $R_1$ and $R_2$ are both methyl groups. Preferably Z is a $C_{1-10}$ alkylene chain e.g. ethylene or octylene, or a $C_{2-4}$ alkylene chain optionally interrupted by a double bond, an oxygen atom, a disulphide group, a $C_{5-7}$ cycloalkyl group, preferably cyclohexyl, or a phenyl group where the cyclohexyl and phenyl groups are conveniently attached to the alkylene chain at the 1,4-positions; or Z represents a phenyl or $C_{5-7}$ cycloalkyl (more preferably cyclohexyl) group.

When $R_5$ represents the group

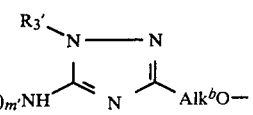

$$R_1'R_2'NAlk'Q'(CH_2)_n'X'(CH_2)_m'NH$$

then more preferably the symbols $R_1'$, $R_2'$, $Alk'$, $Q'$, $n'$, $X'$, $m'$ and $R_3'$ have meanings which are as defined above for the more preferred meanings for the symbols $R_1$, $R_2$, $Alk$, $Q$, $n$, $X$, $m$ and $R_3$ respectively but which in each case, may be the same as or different to the meaning of the latter symbol.

A particularly preferred group of compounds of formula (I) are those of formula (II)

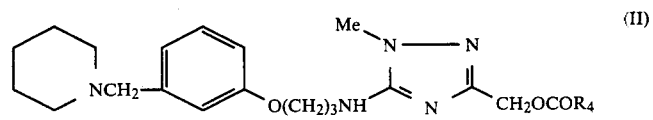

where $R_4$ represents a straight or branched $C_{1-4}$ alkyl group substituted by hydroxy or a benzyloxycarbonylamino group, or the group —$ZCOR_5$ where Z is an unsubstituted alkylene chain containing from 2 to 8 carbon atoms and $R_5$ is ethoxy, or Z is an unsubstituted alkylene chain containing from 2 to 8 carbon atoms or a $C_{2-4}$ alkylene chain interrupted by a phenyl group or Z is a phenyl group or Z is a $C_{2-4}$ alkylene chain containing a double bond and $R_5$ represents a group of the formula

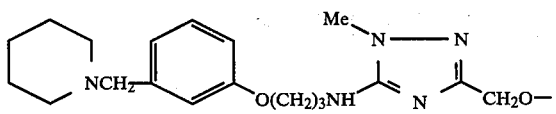

Particularly preferred compounds are:
bis-[[1-methyl-5-[[3-[3-(1-piperidinylmethyl)phenoxy]-propyl]amino]-1H-1,2,4-triazol-3-yl]methyl]butanedioate;
bis-[[1-methyl-5-[[3-[3-(1-piperidinylmethyl)phenoxy]-propyl]amino]-1H-1,2,4-triazol-3-yl]methyl]decandioate;
ethyl 1-methyl-5-[[3-[3-(1-piperidinylmethyl)phenoxy]-propyl]amino]-1H-1,2,4-triazole-3-methyl butanedioate;
E-bis[[1-methyl-5-[[3-[3-(1-piperidinylmethyl)phenoxy]propyl]amino]-1H-1,2,4-triazol-3-yl]methyl]2-butenedioate;
bis-[[1-methyl-5-[[3-[3-(1-piperidinylmethyl)phenoxy]-propyl]amino]-1H-1,2,4-triazol-3-yl]methyl]1,4-benzenedicarboxylate;
[1-methyl-5-[[3-[3-(1-piperidinylmethyl)phenoxy]-propyl]amino]-1H-1,2,4-triazol-3-yl]methyl 2-hydroxypropanoate; and
bis[1-methyl-5-[[3-[3-(1-piperdinylmethyl)phenoxy]-propyl]amino]-1H-1,2,4-triazol-3-yl]methyl 1,4-benzenediacetate;
and physiologically acceptable salts thereof.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, fumarates and benzoates. The compounds of formula (I) and their salts may also form hydrates, which hydrates are also to be considered as part of the invention. The compounds of formula (I) can exhibit tautomerism and the formula is intended to cover all tautomers. Where optical and geometric isomers may exist the formula is intended to cover all diastereoisomers, optical enantiomers and geometric isomers. The term bioprecursors as used herein means compounds which have a structure different to that of the compounds of formula (I) but which, upon administration to the animal or human being, are converted in the body into a compound of formula (I).

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be present in unit dosage form in ampoules, or in multidose containers, with an added preservative. The copositions may take such forms as suspensions, solutions, or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal composition such as suppositories or retention enemas, e.g. containing conventional suppository bases such as cocoa butter or other glycerides.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg to 1 g per day preferably 5 to 250 mg per day dependent upon the condition of the patient.

It will be appreciated that in the methods for the preparation of compounds of formula (I) given below, in certain instances it may be necessary to protect various reactive substituents in the starting material for a particular reaction and subsequently to remove the protecting group. Such protection and subsequent deprotection may be particularly pertinent where $R_1R_2N$ (or $R_1'R_2'N$) contains a primary or secondary amino substituent or where $R_1$ (or $R_1'$) and/or $R_3$ (or $R_3'$) contains a hydroxy alkyl group, or where $R_4$ contains a hydroxy, amino or carboxyl group. Standard protection and deprotection procedures may be employed.

In describing the processes which may be used for preparing the compounds of formula (I) or intermediates useful in the preparation thereof any of $R_1$ to $R_6$, $R_1'$ to $R_6'$, Alk, Alk', Q, Q', n, n', X, X', m, m', $Alk^a$, $Alk^b$ and Z in the various formulae are as defined in formula (I) unless otherwise stated.

Compounds of formula (I) may be prepared by an esterification reaction in which a triazole (III)

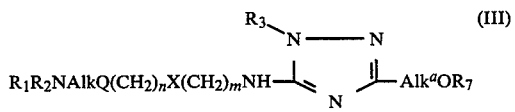

where $R_7$ represents hydrogen, is reacted with an appropriate activated derivative of the acid $R_4CO_2H$. Suitable activated derivatives include those represented by formula (IV)

where L is a leaving group, for example halogen or alkoxy. For example where L is halogen the reaction may be carried out at room temperature, optionally in the presence of a solvent, e.g. pyridine, tetrahydrofuran, acetone, dichloromethane or dimethylformamide, preferably in the presence of a base e.g. pyridine, triethylamine, 4-dimethylaminopyridine or an alkali metal carbonate e.g. potassium carbonate. When L is an alkoxy group e.g. methoxy or ethoxy, the reaction may be carried out by treating the ester (IV) with the triazole (III) at elevated temperature e.g. 100°–170° C., preferably 130°–150° C., in the presence of a base e.g. sodium hydride or a basic catalyst e.g. sodium.

In a modification of the above process compounds of formula (I) which are symmetrical, i.e. compounds in which $R_4$ is the group —$ZCOR_5$ where $R_5$ is the group

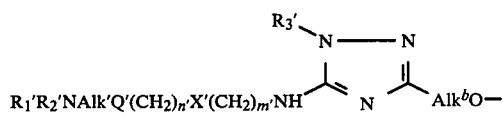

and the groups $R_1'$, $R_2'$, Alk', Q', n', X', m' and $R_3'$ are identical to $R_1$, $R_2$, Alk, Q, n, X, m and $R_3$ respectively and Alk$^a$ is the same as Alk$^b$, may be prepared by reacting a compound of formula (V)

 (V)

in which L and L' are both leaving groups e.g. halogen or $C_{1-3}$ alkoxy, with two equivalents of a triazole of formula (III) in which $R_7$ is hydrogen under the conditions already described.

Compounds of formula (I) in which $R_4$ is the group $ZCOR_5$ where $R_5$ is alkoxy may be prepared by treating a triazole of formula (III) in which $R_7$ represents the group —COZCOL where L is a leaving group e.g. halogen, with an alcohol $R_5H$. Where L is halogen the reaction may be carried out at room temperature, optionally in the presence of a solvent e.g. pyridine, tetrahydrofuran, acetone, dichloromethane or dimethylformamide, preferably in the presence of a base e.g. pyridine, triethylamine or an alkali metal carbonate.

Compounds of formula (I) in which $R_4$ is the group $ZCOR_5$ where $R_5$ is the group

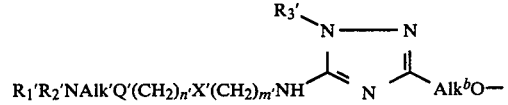

may be prepared by reacting the compound of formula (III) in which $R_7$ represents the group —COZCOL, where L is as defined above, with one equivalent of a hydroxyalkyl triazole of formula (VI)

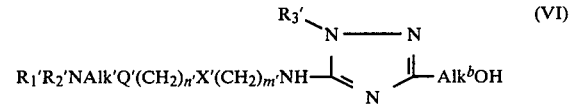 (VI)

under the conditions described above for the reaction of the triazole (III) in which $R_7$ is hydrogen, with the compound (IV). If desired the intermediate triazole (III) in which $R_7$ represents —COZCOL need not be isolated.

In another embodiment of the esterification reaction, compounds of formula (I) may be prepared by reaction of a salt of an acid $R_4CO_2^-X^+$ where $X^+$ is a metal ion such as Na, Ag or a trialkylamino group or more preferably a quaternary ammonium group e.g. $^nBu_4N^+$, with a halide of formula (VII)

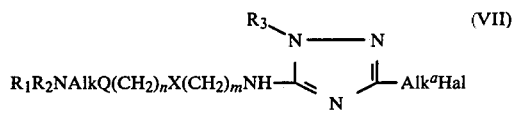 (VII)

where Hal represents a halogen atom e.g. chlorine. The reaction may be carried out in the presence of a solvent e.g. dimethylsulphoxide, acetonitrile or more preferably dimethylformamide, with heating at for example 100° C.

The triazole of formula (III) in which $R_7$ is hydrogen, the hydroxyalkyl triazole of formula (VI) and the compounds of formula (VII) are described in British Patent Specification Publication No. 2047238A and European Patent Specifications Publication Nos. 0027744, 0029303 and 0029306.

Compounds of formula (III) in which $R_7$ represents the group —COZCOL may be prepared by reacting a compound of formula (VIII)

 (VIII)

where L and L' are leaving groups as defined above, with one equivalent of a compound of formula (III) in which $R_7$ represents hydrogen, under the conditions defined above for the reaction of a compound of formula (III) in which $R_7$ is hydrogen and the compound of formula (IV).

The compounds of formulae (IV) and (VIII) in which L and L' are halogen may be prepared from the corresponding acids (L and L' are OH) by conventional procedures for example reacting the acid with thionyl chloride in a solvent, e.g. benzene, at a temperature from room temperature to reflux.

Where the product of any of the above processes is a free base and a salt is required, the salt may be formed in a conventional manner. Thus, for example, a generally convenient method of forming the salts is to mix appropriate quantities of the free base and the acid in an appropriate solvent(s) e.g. an alcohol such as ethanol or an ester such as ethyl acetate.

The invention is illustrated by the following Examples:

PREPARATION 1

1-Methyl-5-[[3-[3-(1-piperidinylmethyl)phenoxy]-propyl]amino]-1H-1,2,4-triazole-3-butanol (a) Methyl 5-[[[1-methyl-2-(phenylmethylene)hydrazino](methylthio)methylene]amino]-5-oxopentanoate Methyl 4-(chloroformyl)butyrate (31.2 g) was added dropwise during 1 h at 20° to a stirred solution of methyl 1-methyl-2-(phenylmethylene)hydrazine carboximidothioate (3.60 g) and triethylamine (20.0 g) in dichloromethane (100 ml). The pale yellow suspension was stirred at 20° C. for 16 h. A further portion of methyl 4-(chloroformyl)butyrate (6.2 g) and triethylamine (4.0 g) was added and stirring continued for a further 1 h. Water (100 ml) was added, the organic layer separated and washed successively with saturated aqueous sodium bicarbonate and water, dried, and evaporated to give a brown solid (53.6 g). This solid was recrystallised from ether to give the title compound (30.9 g) as a pale yellow solid m.p. 69°-70°.

(b) Potassium
1-Methyl-5-[[3-[3-(1-piperidinylmethyl)phenoxy]-propyl]amino]-1H-1,2,4-triazole-3-butanoate 3-[3-(1-piperidinylmethyl)phenoxy]propanamine (7.1 g) in toluene (50 ml) was added dropwise to a solution of methyl 5-[[[1-methyl-2-(phenylmethylene)hydrazino](methylthio)methylene]amino]-5-oxo-pentanoate (10.0 g) in toluene (200 ml) at 20°. The solution was stirred at 20° for 3 h, 5N hydrochloric acid (28 ml) added, and stirring continued at 20° for 18 h. The acidic layer was separated, basified (pH 8–9) with potassium carbonate and extracted with ethyl acetate. The aqueous layer was saturated with potassium carbonate and extracted with 2-propanol. The extract was dried and evaporated to give the title compound (16.0 g) as a crude solid.

(c) Ethyl
1-Methyl-5-[[3-[3-(1-piperidinylmethyl)phenoxy]-propyl]amino]-1H-1,2,4-triazole-3-butanoate Potassium 1-methyl-5[[3-[3-(1-piperidinylmethyl)phenoxy]propyl]amino]-1H-1,2,4-triazole-3-butanoate (2.0 g) and concentrated sulphuric acid (1 ml) in anhydrous ethanol (200 ml) was heated under reflux for 16 h. The suspension was filtered, the filtrate evaporated, and saturated aqueous sodium bicarbonate (50 ml) added. The mixture was extracted with ethyl acetate, the extract washed with brine, dried, and evaporated to give the title compound (1.0 g) as an oil.

(d)
1-Methyl-5-[[3-[3-(1-piperidinylmethyl)phenoxy]-propyl]amino]-1H-1,2,4-triazole-3-butanol Lithium aluminium hydride (1.41 g) was added to a solution of ethyl 1-methyl-5-[[3-[3-(1-piperidinylmethyl)phenoxy]propyl]amino]-1H-1,2,4-triazole-3-butanoate (3.3 g) in anhydrous tetrahydrofuran (100 ml), under nitrogen, and the mixture stirred at 20° for 18 h. Successively, water (1.4 ml), 5N sodium hydroxide (1.4 ml) and water (3 ml) were added, the mixture was filtered and the filtrate evaporated to give an oil (3.1 g). The oil was chromatographed on silica using dichloromethane:ethanol:0.88 ammonia 70:8:1 as eluent to give the title compound (2.4 g) as a green oil.

N.m.r. (CDCl$_3$):
2.82,t,(1H);3.0–3.4,m,(3H);5,57,t,(1H);
5.92,t,(2H);6.3–6.7,m+s+s, (9H);7.1,s(br.),(1H);7.4,t,(2H);7.6,m,(4H);7.9,m,(2H);8.1–8.7,m,(10H).

EXAMPLE 1

Bis-[[1-methyl-5-[[3-[3-(1-piperidinylmethyl)phenoxy]-propyl]amino]-1H-1,2,4-triazol-3-yl]methyl]butanedioate To a stirred mixture of butanedioyl dichlorite (0.19 g) and pyridine (3 ml) was added portionwise 1-methyl-5-[[3-[3-(1-piperidinylmethyl)phenoxy]propyl]amino]-1H-1,2,4-triazole-3-methanol (0.8 g). After stirring at room temperature for 16.5 h, water (10 ml) and anhydrous sodium carbonate (1 g) were added and the solution evaporated to dryness with the aid of ethanol (3×10 ml). To the residue was added ethyl acetate (60 ml), excess anhydrous sodium carbonate and decolourising charcoal. After 2 h, the mixture was filtered, the residue washed with hot ethyl acetate (4×15 ml) and the filtrate evaporated to give a white residue. This was crystallised from ethyl acetate to give the title compound (0.3 g), m.p. 116°–118°.

Found: C, 63.0: H, 7.5; N, 17.4; $C_{42}H_{60}N_{10}O_6$ requires: C, 63.0; H, 7.6; N, 17.5%.

In a similar manner was prepared: Bis-[[1-methyl-5-[[3-[3-(1-piperidinylmethyl)phenoxy]propyl]amino]-1H-1,2,4-triazol-3-yl]methyl]decandioate (0.54 g), m.p. 80°–81.5° from 1-methyl-5-[[3-[3-(1-piperidinylmethyl)-phenoxy]propyl]amino]-1H-1,2,4-triazole-3-methanol (2.16 g) and decanedioyl dichloride (0.79 g) in pyridine (8 ml) at room temperature for 22 h.

Found: C, 65.0; H, 8.2; N, 15.7; $C_{48}H_{72}N_{10}O_6$ requires: C, 65.1; H, 8.2; N, 15.8%.

EXAMPLE 2(a)

Bis-[1-Methyl-5-[[3-[3-(1-piperidinylmethyl)phenoxy]-propyl]amino]-1H-1,2,4-triazol-3-yl]methyl 1,4-benzenediacetate A solution of 1-methyl-5-[[3-[3-(1-piperidinylmethyl)-phenoxy]propyl]amino]-1H-1,2,4-triazole-3-methanol (3.0 g), triethylamine (0.86 g), and benzene-1,4-diacetyl chloride (1.0 g) in anhydrous dichloromethane (50 ml) was stirred at 20° for 18 h. Water (50 ml) was added and the dichloromethane layer separated, dried and evaporated to give an oil (2.3 g). This was chromatographed on alumina using ethyl acetate:methanol (19:1) to give the title compound (1.0 g) as a white solid m.p. 121°–122°, recrystallised from ethyl acetatecyclohexane.

Found: C, 65.9; H, 7.2; N, 15.5; $C_{48}H_{64}N_{10}O_6$ requires: C, 65.7; H, 7.4; N, 16.0%.

Similarly prepared by this procedure were:
(b) From 1-methyl-5-[[3-[3-(1-piperidinylmethyl)-phenoxy]propyl]amino]-1H-1,2,4-triazole-3-methanol (3.59 g), triethylamine (1.11 g) and phenylmethyl N-(chloroacetyl) carbamate (2.45 g) in dichloromethane (60 ml) except that the crude product was chromatographed on alumina using methanol:ethyl acetate (2:98) as eluent and then crystallised from ethyl acetate-cyclohexane, was prepared [1-methyl-5-[[3-[3-(1-piperidinylmethyl)phenoxy]propyl]amino]-1H-1,2,4-triazol-3-yl]methyl [[(phenylmethoxy) carbonyl]amino]acetate (1.9 g) as a white solid m.p. 95°–96°.

Found: C, 63.3; H, 7.0; N, 14.9; $C_{29}H_{38}N_6O_5$ requires: C, 63.3; H, 7.0; N, 15.2%.

(c) From 1-methyl-5-[[3-[3-(1-piperidinylmethyl)-phenoxy]propyl]amino]-1H-1,2,4-triazole-3:methanol (2.16 g), triethylamine (0.64 g) and (E)-2-butenedioyl dichloride (0.48 g) in dichloromethane (30 ml), except that the crude product was crystallised from 4-methyl-2-pentanone, was prepared (E)-bis-[1-methyl-5-[[3-[3-(1-piperidinylmethyl)phenoxy]propyl]amino]-1H-1,2,4-triazol-3-yl]methyl 2-butenedioate hemihydrate (0.379 g) as a white solid m.p. 134°–135°.

Found: C, 62.5; H, 7.2; N, 17.1; $C_{42}H_{58}N_{10}O_6 \cdot \frac{1}{2}H_2O$ requires: C, 62.4; H, 7.4; N, 17.3%.

(d) From 1-methyl-5-[[3-[3-(1-piperidinylmethyl)-phenoxy]propyl]amino]-1H-1,2,4-triazole-3-methanol (2.16 g), triethylamine (0.91 g) and benzene-1,4-dicarbonyl chloride (0.91 g) in dichloromethane (20 ml), except that the crude product was chromatographed on silica using methanol:0.88 ammonia (200:1) as eluent, was prepared bis-[1-methyl-5-[[3-[3-(1-piperidinylmethyl)-phenoxy]propyl]amino]-1H-1,2,4-triazol-3yl]methyl 1,4-benzene-dicarboxylate hemihydrate (0.38 g) m.p. 127°–129° crystallised from ethyl acetate.

Found: C, 64.5; H, 7.0; N, 16.1; $C_{46}H_{60}N_{10}O_6.\frac{1}{2}H_2O$ requires: C, 64.4; H, 7.2; N, 16.3%.

(e) From 5-[[3-[3-[(dimethylamino)methyl]phenoxy]-propyl]amino]-1-methyl-1H-1,2,4-triazole-3-methanol (1.8 g), 2,2'-oxybis[acetyl chloride] (0.50 g) and triethylamine (0.80 ml) in dichloromethane (20 ml), except that the product was crystallised from methyl acetate and light petroleum (b.p. 60°–80°), was prepared bis-[5-[[3-[3-[(dimethylamino)methyl]phenoxy]propyl]amino]-1-methyl-1H-1,2,4-triazol-3yl]methyl 2,2'-oxybis[acetate] (0.07 g as a white solid m.p. 96°–98°.

N.m.r. (CDCl₃): 2.75,t,(1H); 3.0–3.2,m,(3H); 4.92,s,(2H); 5.53,t,(1H); 5.68,s,(2H); 5.85,t,(2H); 6.37,q,(2H); 6.45,s,(3H); 6.60,s,(2H); 7.74,s,(2H); 7.85,m,(2H).

(f) From 1-methyl-5-[[3-[3-(1-piperidinylmethyl)-phenoxy]propyl]amino]-1H-1,2,4-triazole-3-butanol (1.7 g) containing ethanol (50 mg), triethylamine (0.47 g) and 1,4-benzene dicarbonyl chloride (0.45 g) in dichloromethane (25 ml), except that the crude product was chromatographed on alumina using ether:ethyl acetate:-methanol (50:50:1) as an eluent, was prepared ethyl [1-methyl-5-[[3-[3-(1-piperidinylmethyl)phenoxy]-propyl]amino]-1H-1,2,4-triazol-3-yl]butyl 1,4-benzenedicarboxylate (0.44 g) as a clear gum.

Found: C, 66.8; H, 7.5; N, 11.9; $C_{32}H_{43}N_5O_5$ requires: C, 66.5; H, 7.5; N 12.1%.

N.m.r. (CDCl₃): 1.90,s,(4H); 2.79,t,(1H); 3–3.35,m,(3H), 5.4–5.7, q+t+bt,(5H); 5.88,t,(2H); 6.38–6.55, q+s+s,(7H); 7.30,bt,(2H); 7.60–8.10,m+m+m,(10H); 8.3–8.7,m+t,(9H).

EXAMPLE 3

Ethyl 1-methyl-5-[[3-[3-(1-piperidinylmethyl)phenoxy]-propyl]amino]-1H-1,2,4-triazole-3-methyl butanedioate A mixture of 1-methyl-5-[[3-[3-(1-piperidinylmethyl)-phenoxy]propyl]amino]-1H-1,2,4-triazole-3-methanol (0.72 g), diethyl butanedioate (1.75 g) and sodium hydride (20 mg) was heated at 140°–150° for 5.5 hours. Ether (70 ml) was added, the suspension filtered and the filtrate evaporated in vacuo. The oily residue was dissolved in ethyl acetate (30 ml) and the solution extracted with 2M hydrochloric acid (15 ml). The acid extract was washed with ethyl acetate (10 ml) and basified with sodium carbonate. The aqueous mixture was extracted with ethyl acetate (2×20 ml), the combined extracts dried (Na₂CO₃) and decolourised (charcoal). The mixture was filtered and the filtrate evaporated in vacuo to give an oil which was chromatographed on silica using acetone to give an oil (0.15 g), which slowly solidified, consisting of the title compound, m.p. 64°–67°.

N.m.r. (CDCl₃): 2.80,t,(1H); 3.00–3.30,m,(3H); 5.00,s,(2H); 5.50,t,(1H); 5.70–6.10,t+q,(4H); 6.40,q,6.47,s,6.60s,(7H); 7.35,AA'BB'(4H); 7.65m,7.90,m,(6H); 8.50,m,8.77,t,(9H).

Similarly prepared by this procedure were:

(b) From 5-[[2-[[[5-[(dimethylamino)methyl]-4-methyl-2-furanyl]methyl]thio]ethyl]amino]-1-methyl-1H-1,2,4-triazole-3-methanol (1.0 g), diethyl, 3,3'-bis (propanoate) (3.9 g) and sodium hydride (36 mg), except that the crude product was chromatographed on alumina using ether:ethyl acetate:methanol (50:50:2) as an eluent, was prepared [[5-[[2-[[[5-[(dimethylamino)-methyl]-4-methyl-2-furanyl]methyl]thio]ethyl]amino]-1-methyl-1H-1,2,4-triazol-3-yl]methyl]ethyl 3,3'-dithi-obis[propanoate]hemihydrate (0.4 g) as a brown gum.

Found: C, 49.7; H, 6.6; N, 12.6; $C_{23}H_{37}N_5O_4S_3.\frac{1}{2}H_2O$ requires: C, 50.0; H, 6.9; N, 12.7%.

N.m.r. (CDCl₃): 3.95,s,(1H); 4,95,s,(2H); 5,27,t,(1H); 5.82,q,(2H); 6.30,s,(2H); 6.40,s,(3H); 6.52,q,(2H); 6.60,s,(2H); 7.0–7.4,m,(10H); 7.74,s,(6H); 8.01,s,(3H); 8.71,t,(3H).

(c) From 1-methyl-5-[[3-[3-(1-piperidinylmethyl)-phenoxy]propyl]amino]-1H-1,2,4-triazole-3-methanol (2.0 g), dimethyl 1,4-cyclohexanedicarboxylate (cis-trans mixture) (5.6 g) and sodium hydride (0.1 g), except that the crude product (1.8 g) was chromatographed on alumina using ether:ethyl acetate:methanol 50:50:1 as eluent, was prepared methyl [1-methyl-5-[[3-[3-(1-piperidinylmethyl)phenoxy]propyl]amino]-1H-1,2,4-triazol-3-yl]methyl 1,4-cyclohexanedicarboxylate (0.52 g) as a colourless oil.

N.m.r. (CDCl₃): 2.83,t,(1H); 3.06–3.4,m,(3H); 5.12,s,(2H); 5.6,t,(1H); 6.0,t,(2H); 6.4,s,(3H); 6.55,s,(3H); 6.65,q,(2H); 6.4–6.7,s,(2H); 7.4–8.9,m,(22H).

T.l.c. Alumina; ether:ethyl acetate:methanol 50:50:2. Rf 0.6.

EXAMPLE 4

[1-Methyl-5-[[3-[3-(1-piperidinylmethyl)phenoxy]-propyl]amino]-1H-1,2,4-triazol-3-yl]methyl 2-hydroxypropanoate A solution of 1-methyl-5-[[3-[3-(1-piperidinylmethyl)-phenoxy]propyl]amino]-1H-1,2,4-triazole-3-methanol (2.38 g) in thionyl chloride (10 ml) was heated under reflux for 15 min, and evaporated. The residue was treated with saturated aqueous sodium bicarbonate until effervescence ceased, sodium carbonate (3 g) was added, and the mixture extracted with ethyl acetate. The extract was dried and evaporated to give an oil (2.84 g) which was dissolved in dimethylformamide (10 ml) and added dropwise to a stirred solution of tetra n-butyl ammonium 2-hydroxypropanoate, prepared by evaporating to dryness a mixture of lactic acid (0.54 g) and tetra n-butyl ammonium hydroxide (40% w-w, 3.9 g), in dimethylformamide (10 ml), and the mixture heated at 100° for 3 h. The solution was evaporated, extracted with ethyl acetate and the extract washed with water, dried and evaporated. The residue (2.0 g) was chromatographed on silica using dichloromethane:ethanol:0.88 ammonia 50:8:1 as eluent to give the title compound (1.31 g) as a gum.

N.m.r. (CDCl₃): 2.8,t,(1H); 3.0–3.3,m,(3H); 4,97,m,(2H); 5.42,t,(1H); 5.7,q,(1H); 5.92,t,(2H); 6.4,q,(2H); 6.47,s,(3H); 6.6,s,(2H), 6.8,s,(br),(1H); 7.7–7.9,m,(6H); 8.5,m,(6H); 8.6,d,(3H).

T.l.c. Silica; dichloromethane:ethanol:0.88 ammonia. Rf 0.62.

EXAMPLE 5

Examples of pharmaceutical compositions according to the invention are as follows:

| (a) TABLETS | mg/tablet | mg/tablet |
|---|---|---|
| Active ingredient | 20.0 | 40.0 |
| Microcrystalline cellulose BPC | 99.5 | 199.0 |
| Magnesium stearate B.P. | 0.5 | 1.0 |

| (a) TABLETS | mg/tablet | mg/tablet |
|---|---|---|
| Compression weight | 120.0 | 240.0 |

The drug is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

| (b) CAPSULES | mg/capsule |
|---|---|
| Active ingredient | 20.0 |
| *Sta-Rx 1500 Starch | 79.5 |
| Magnesium Stearate B.P. | 0.5 |
| Fill weight | 100.00 |

*A form of directly compressible starch supplied by Colorcon Ltd, Orpington, Kent.

The active ingredient is sieved through a 250 μm sieve and blended with other materials. The mix is filled into No. 3 hard gelatin capsules using a suitable filling machine. Other doses may be prepared by increasing the fill weight and if necessary changing the size of the capsule to accommodate the increase.

We claim:

1. A compound of formula (I)

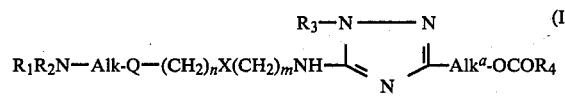

or a physiologically acceptable salt or hydrate thereof in which $R_1$ represents $C_{1-14}$ alkyl, $C_{3-8}$ cycloalkyl, $C_{3-6}$ alkenyl, $C_{3-6}$ alkynyl, aryl $C_{1-6}$ alkyl, heteroaralkyl wherein the heteroaryl portion is thienyl, pyrrolyl, pyridyl, furyl or thiazolyl which may be unsubstituted or substituted by $C_{1-3}$ alkyl, $C_{1-3}$ alkoxy, hydroxy $C_{1-6}$ alkyl, amino $C_{1-6}$ alkyl, $C_{1-6}$ alkylamino $C_{1-6}$ alkyl, di-$C_{1-6}$ alkyl amino $C_{1-6}$ alkyl or halogen, the alkyl portion of the heteroaralkyl ring is a straight or branched $C_{1-4}$ alkyl chain, and the heteroaryl ring is linked to the alkyl portion through a carbon atom; trifluoro $C_{1-6}$ alkyl or $C_{1-6}$ alkyl substituted by hydroxy, $C_{1-6}$ alkoxy, amino, $C_{1-6}$ alkylamino, di $C_{1-6}$ alkylamino or $C_{3-8}$ cycloalkyl; and $R_2$ represents hydrogen or $C_{1-4}$ alkyl; or $R_1$ and $R_2$ may together with the nitrogen atom to which they are attached form a piperidino, morpholino, 4-methylpiperidino, pyrrolidino, hexamethylenimino or tetrahydropyridino group; Alk represents a straight or branched alkylene chain of 1 to 6 carbon atoms; Q represents a furan or thiophen ring in which incorporation into the rest of the molecule is through bonds at the 2- and 5-positions, the furan or thiophen ring optionally bearing a further substituent $R_6$ adjacent to the group $R_1R_2N$-Alk; or Q repesents a thiophen ring in which incorporation into the rest of the molecule is through bonds at the 2- and 4-positions, the thiophen ring optionally bearing a further substituent $R_6$ adjacent to the group $R_1R_2N$-Alk with the proviso that when the group $R_1R_2N$Alk is in the 4-position then the group $R_6$ is in the 5-position; or Q represents a benzene ring in which incorporation into the rest of the molecule is through bonds at the 1- and 3- or 1- and 4-positions;

$R_6$ represents halogen or $C_{1-4}$ alkyl which may be substituted by hydroxy or $C_{1-4}$ alkoxy;

X represents oxygen, sulphur, —NH—, methylene or a bond;

n represents zero, 1 or 2; and m represents an integer from 2 to 5; with the proviso that when X represents —NH— then Q is a benzene ring;

$R_3$ represents hydrogen, $C_{1-6}$ alkyl, $C_{3-6}$ alkenyl, ar $C_{1-6}$ alkyl, or $C_{2-6}$ alkyl substituted by hydroxy or $C_{1-6}$ alkoxy;

$Alk^a$ represents a straight or branched alkylene chain containing from 1 to 6 carbon atoms;

$R_4$ represents the group —ZCOR$_5$ where $R_5$ represents hydroxy or $C_{1-6}$ alkoxy or the group

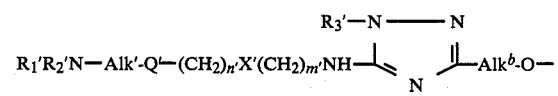

in which the symbols $R_1'$, $R_2'$, Alk', Q', n', X', m' and $R_3'$ have meanings which are as defined above for the symbols $R_1$, $R_2$, Alk, Q, n, X, m and $R_3$ respectively but which, in each case, may be the same as or different to the meaning of the latter symbol;

$Alk^b$ represents a straight or branched alkylene chain containing from 1 to 6 carbon atoms;

Z represents an alkylene chain containing from 1 to 16 carbon atoms optionally substituted by one or two $C_{1-3}$ alkyl groups and optionally containing a double or triple bond; or optionally interrupted by an oxygen or sulphur atom, or by a disulphide (S-S) group; or optionally interrupted by a $C_{3-8}$ cycloalkyl or a phenyl group, or Z represents a $C_{3-8}$ cycloalkyl or a phenyl group; or $R_4$ represents a $C_{1-6}$ straight or branched hydroxyalkyl group, optionally substituted by hydroxy or amino, or an amino $C_{1-6}$ alkyl group optionally substituted by amino, SH, $CO_2H$, phenyl or 4-hyroxyphenyl; and wherein the term aryl as a group or part of a group means phenyl or phenyl substituted with one or more $C_{1-3}$ alkyl or alkoxy groups or halogenatoms.

2. A compound according to claim 1, in which:

$R_1$ represents $C_{1-8}$ alkyl, $C_{1-4}$ alkyl substituted by a trifluoromethyl group, $C_{2-4}$ alkyl substituted by hydroxy or a di $C_{1-3}$ alkylamino group, $C_{5-7}$ cycloalkyl, $C_{3-5}$ alkenyl, phenyl $C_{1-3}$ alkyl, or a heteroaryl $C_{1-3}$ alkyl group where the heteroaryl ring contains one heteroatom;

$R_2$ represents hydrogen or methyl; or $R_1R_2N$ represents a piperidino, morpholino, 4-methylpiperidino, pyrrolidino, hexamethylenimino or tetrahydropyridino group;

Alk represents methylene;

Q represents a benzene ring incorporated into the rest of the molecule through the bonds at the 1- and 3-positions; or a furan ring incorporated into the rest of the molecule through bonds at the 2- and 5-positions optionally bearing a substituent $R_6$ adjacent to the group $R_1R_2N$Alk where $R_6$ is $C_{1-4}$ alkyl; or a thiophene ring incorporated into the rest of the molecule through bonds at the 2- and 4-positions with the substituent $R_1R_2N$Alk in the 2-position; with the provisos that when Q is a benzene ring as just defined, then n is zero, X is oxygen, and m is 3 or 4; and when Q is a furan or thiophene ring as just defined, then n is 1, X is sulphur and m is 2, or X is oxygen and m is 3;

$R_3$ represents hydrogen or $C_{1-4}$ alkyl;

$Alk^a$ represents a straight or branched alkylene chain containing 1 to 4 carbon atoms; and $R_4$ represents a $C_{1-4}$ straight or branched hydroxyalkyl group or a $C_{1-4}$ aminoalkyl group in which the amino group is in the α-position relative to the ester moiety, optionally substituted by amino, SH, $CO_2H$, phenyl or 4-hydroxyphenyl or $R_4$ represents the group $-ZCOR_5$ where Z represents a cyclohexyl group or an unsubstituted alkylene chain containing 1 to 16 carbon atoms, and $R_5$ represents hydroxy or $C_{1-4}$ alkoxy; or Z represents a phenyl group or an unsubstituted alkylene chain containing 1 to 16 carbon atoms optionally containing a double bond or optionally interrupted by either an oxygen atom or a disulphide group or a phenyl group, and $R_5$ represents a group

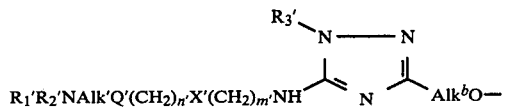

in which the symbols $R_1'$, $R_2'$, Alk', Q', n', X', m' and $R_3'$ have meanings which are as defined above for the symbols $R_1$, $R_2$, Alk, Q, n, X, m and $R_3$ respectively but which, in each case, may be the same as or different to the meaning of the latter symbol, and $Alk^b$ represents a straight or branched alkylene chain containing 1 or 2 carbon atoms.

3. A compound according to claim 2 in which $R_1$ and $R_2$ are both methyl or, together with the nitrogen atom to which they are attached, form a pyrrolidino, piperidino or hexamethylenimino group;

Alk represents methylene and $R_3$ is hydrogen or methyl and; either n is zero, X is oxygen, m is 3 or 4 and Q is a benzene ring linked through the 1- and 3-positions; or n is 1, X is sulphur, m is 2 and Q is furan linked through the 2- and 5-positions with optionally a methyl substituent on the carbon atom adjacent to the group $R_1R_2NCH_2-$ or Q is a thiophen ring linked through the 2- and 4-positions with the group $R_1R_2NCH_2-$ in the 2-position; with the proviso that when Q is other than a benzene ring then $R_1$ and $R_2$ are both methyl groups.

4. A compound according to claim 3 in which n is zero, X is oxygen, m is 3 or 4 and Q is a benzene ring linked through the 1- and 3-positions.

5. A compound according to claim 2 in which $R_4$ represents the group $-ZCOR_5$ where $R_5$ represents hydroxy or alkoxy or the group

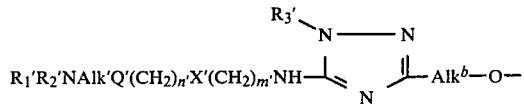

in which $R_1'$ and $R_2'$ are both methyl or, together with the nitrogen atom to which they are attached, form a pyrrolidino, piperidino or hexamethylenimino group;

Alk' represents methylene and $R_3'$ is hydrogen or methyl and; either n' is zero, X' is oxygen, m' is 3 or 4 and Q' is a benzene ring linked through the 1- and 3-positions; or n' is 1, X' is sulphur, m' is 2 and Q' is furan linked through the 2- and 5-positions with optionally a methyl substituent on the carbon atom adjacent to the group $R_1'R_2'NCH_2-$ or Q' is a thiophen ring linked through the 2- and 4-positions with the group $R_1'R_2'NCH_2-$ in the 2-position; with the proviso that when Q' is other than a benzene ring then $R_1'$ and $R_2'$ are both methyl groups.

6. A compound according to claim 1 of formula (II)

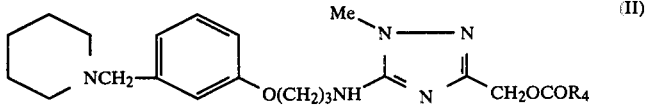

(II)

where $R_4$ represents a straight or branched $C_{1-4}$ alkyl group substituted by hydroxy or a benzyloxycarbonylamino group, or the group $-ZCOR_5$ where Z is an unsubstituted alkylene chain containing from 2 to 8 carbon atoms and $R_5$ is ethoxy, or Z is an unsubstituted alkylene chain containing from 2 to 8 carbon atoms or a $C_{2-4}$ alkylene chain interrupted by a phenyl group or Z is a phenyl group or Z is a $C_{2-4}$ alkylene chain containing a double bond and $R_5$ represents a group of the formula

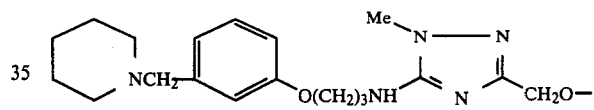

7. Bis-[[1-methyl-5-[[3-[3-(1-piperidinyl]methyl, phenoxy]propyl]amino]-1H-1,2,4-triazol-3-yl]methyl]butanedioate;

bis-[[1-methyl-5-[[3-[3-(1-piperidinylmethyl)phenoxy]-propyl]amino]-1H-1,2,4-triazol-3-yl]methyl]decandioate;

ethyl 1-methyl-5-[[3-[3-(1-piperidinylmethyl)phenoxy]-propyl]amino]-1H-1,2,4-triazole-3-methyl butanedioate;

E-bis[[1-methyl-5-[[3-[3-(1-piperidinylmethyl)phenoxy]propyl]amino]-1H-1,2,4-triazol-3-yl]methyl]2-butenedioate;

bis-[[1-methyl-5-[[3-[3-(1-piperidinylmethyl)phenoxy]-propyl]amino]-1H-1,2,4-triazol-3-yl]methyl]1,4-benzenedicarboxylate;

[1-methyl-5-[[3-[3-(1-piperidinylmethyl)phenoxy]-propyl]amino]-1H-1,2,4-triazol-3-yl]methyl 2-hydroxypropanoate; and bis[1-methyl-5-[[3-[3-(1-piperidinylmethyl)phenoxy]-propyl]amino]-1H-1,2,4-triazol-3-yl]methyl 1,4-benzene diacetate or a physiologically acceptable salt thereof.

8. A pharmaceutical composition for the treatment of conditions mediated through histamine $H_2$-receptors which comprises an effective amount of a compound as claimed in claim 1 together with at least one inert pharmaceutically acceptable carrier or diluent.

9. A method of treating a condition mediated through histamine $H_2$-receptors which comprises administering to a patient an effective amount of a compound as defined in claim 1 to relieve said condition.

* * * * *